Figure 1:
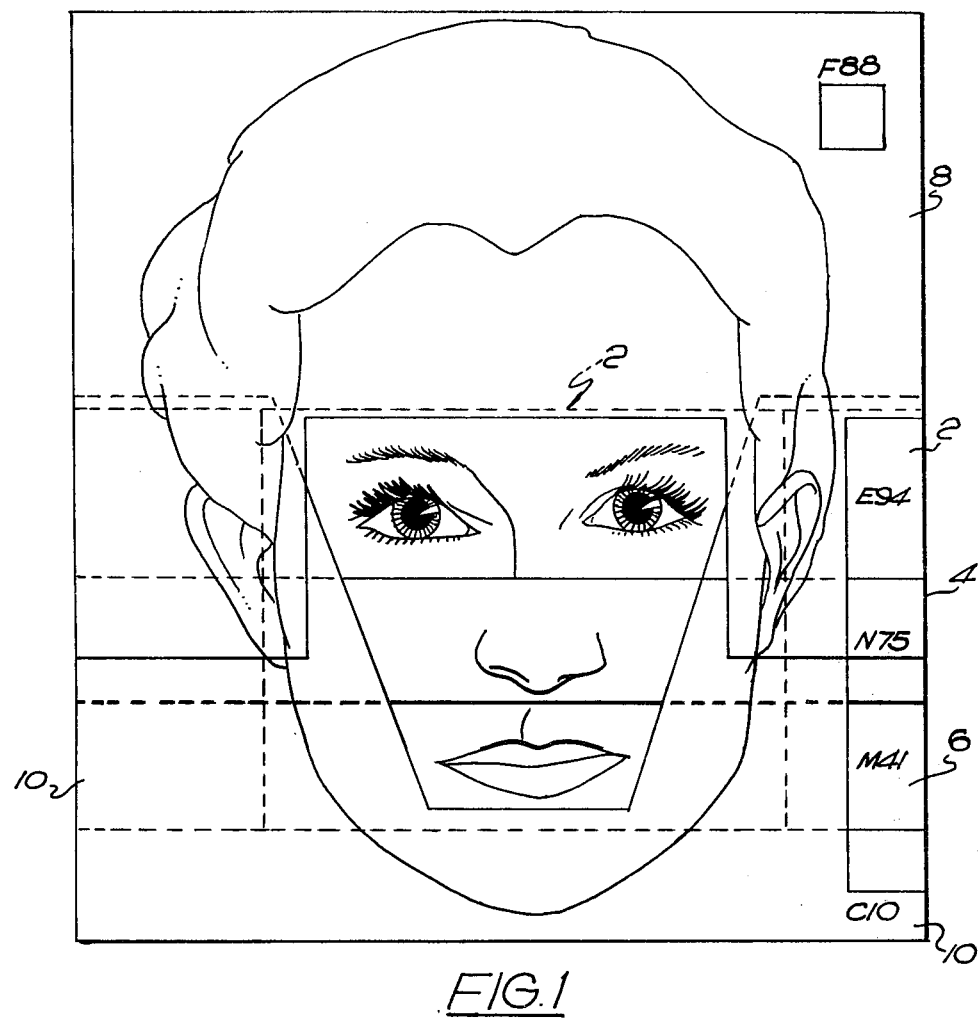

United States Patent [19]

Ryan

[11] 4,045,883
[45] Sept. 6, 1977

[54] IDENTIFICATION KIT AND METHOD

[76] Inventor: Wilfred Edward Ryan, 47 Lower Green Road, Pembury, Tunbridge Wells, Kent, England

[21] Appl. No.: 352,894

[22] Filed: Apr. 20, 1973

Related U.S. Application Data

[63] Continuation-in-part of Ser. No. 852,855, Aug. 25, 1969, abandoned.

[51] Int. Cl.² .............................................. G09B 1/16
[52] U.S. Cl. ...................................................... 35/28
[58] Field of Search ......................... 35/26, 28, 53, 59; 283/7; 273/157 R

[56] References Cited

U.S. PATENT DOCUMENTS

| 609,347 | 8/1898 | Von Holzhausen | 273/157 R |
| 2,293,441 | 8/1942 | Meyer | 35/53 |
| 2,919,502 | 1/1960 | Henry | 35/59 |
| 2,974,426 | 3/1961 | McDonald | 35/26 |

FOREIGN PATENT DOCUMENTS 1,195,057 6/1965 Germany ................................. 35/28

OTHER PUBLICATIONS

W. R. Hopper, "Photo-Fit-The Penry Facial Identification Technique" J. Forensic Sci. Soc. (1973), 13 p. 77 only.

Primary Examiner—Harland S. Skogquist

[57] ABSTRACT

An identification system intended primarily for use by Police Forces and Police Departments and other organizations in the field of criminal investigation, the identification system making use of first and second pluralities of photographic facial portions, each portion bearing one or more facial characteristics, said first and second pluralities respectively incorporating portions to enable full front face views and corresponding profile face views to be assembled, the portions in said first and second pluralities being in the same geometric scale and each carrying indicia so that the selection of a photographic portion from one of said pluralities automatically enables the selection of the corresponding photographic portion from the other of said pluralities, whereby both a full front face photographic assembly and a corresponding profile photographic assembly of the facial features of a recollected person can be composed by a witness who recalls said person.

2 Claims, 2 Drawing Figures

IDENTIFICATION KIT AND METHOD

This invention relates to a method and apparatus for use in assembling a picture of a person recollected from memory, and the present application constituted a Continuation-in-Part of my now abandoned application Ser. No. 852,855 filed 8/25/69.

In said Patent Application Ser. No. 852,855 the structure disclosed therein for comparison with the imaginary person was shown but all the advantages and successes of the structure according to the invention were not set forth to support unobviousness over the prior art and unobviousness to those skilled in the art in the market place of law enforcement throughout the world, and to support the unexpected results, those advantages and successes not having been in the earlier application. This evidence could not have been presented to the Examiner in the earlier application because the information was not available or could not have been gathered until after final rejection of said earlier application.

The method and apparatus of the present application is primarily, although not exclusively, intended for use by Police Forces and Police Departments and other organisations in the field of criminal investigation, and the invention relates in particular to an improved method and apparatus which are used for assembling a picture, using photographic parts, of a person recollected from the memory of a person viewing the assembly.

My identification system as set forth in said application Ser. No. 852,855 was broader in respect of the fact that it included pictorial representations beyond photographic, and the present invention is restricted to, and to the use of, photographic impressions.

Identification systems for criminal investigation purposes and for other purposes are known.

One such system, in the form of a game apparatus, involved the assembly of several pieces into a picture of a well-known person so that the user could form from this picture object lessons in character study. The game apparatus of this system comprises a series of trays, and portraits made in separable pieces, the trays each having depressions into which the pieces of the portrait are adapted to fit, the separable pieces of the various portraits being alike in shape so as to permit interchanging of corresponding parts of the several portraits. The portraits of this system are profile views of well-known persons. The pieces of this game apparatus are exactly alike in configuration so as to permit a ready interchange from one portrait to another.

Whilst this prior game apparatus utilises separable pieces to form different profile views, the game apparatus did not foresee the possibility of having corresponding front face views so that as the profile view was changed by substitution of one or more pieces so the corresponding front face view could be changed by substitution of the corresponding pieces. Nor did this game apparatus foresee that the apparatus could be used for criminal indentification purposes, and there is no necessity for the user of the game apparatus to recollect a face from memory and then to construct that face.

In another known system, useful exclusively in experimenting with different combinations of feminine appearances, use was made of a base card or sheet onto which a plurality of display means are selectively superposable, these display means, in the form of sheets of varying delineations being laid one over the other so as to alter the overall facial appearance.

The facial characteristics on said display means of this apparatus are line drawings, and not photographic impressions, and whilst the apparatus shows the use thereof in relation to profile views, there is no suggestion that the profile and front face views shall correspond one with the other, or that the apparatus could be used for criminal identification purposes.

Once again there is no question of the user of this known device having to recall a person's face from the parts of the device.

In yet another prior known arrangement use is made of a device having stacks of line drawings which are placed in a frame in structural relationship to be representative of a human face. Five stacks of cards are located in the device, each card bearing a line drawing of a facial feature, and the cards in each stack bearing a different form of the same facial feature. The facial features displayed in the device may be changed by sliding out of the device that facial feature not required so as to reveal another form of the same facial feature.

This device, unlike the present invention, uses line drawings to represent the facial feature. The present invention involves the use of photographic parts and the method of utilisation is different in the formation of a recollected face.

In still another prior arrangement, relating to recording systems, use was made of line drawings applied to a card. The card showed cranial characteristics in dotted line formation, both in front and profile, and to compile a representation of a human face, or one desired to be represented, it was necessary to draw onto the card, in correct position, the several facial features. The drawing of the facial features onto the card was aided by the provision of guide lines on the card. In this prior arrangement there is no facility, apart from erasure of the lines drawn onto the card, of making adjustments to the views on the card. This apparatus was to be used in establishing or as an aid in establishing the characteristics of the person being drawn, and it is impossible to see how this apparatus could be useful in criminal identification techniques. The apparatus does not use parts of photographic impressions, andno requirement on the part of the user to recollect a person's face is called for.

Still another prior known device relates to a picture making device for compositing pictures in which an operator may select any one of a number of different portrayals or representations of the component parts of the composite picture and the selected component parts may be assembled in proper relationship so as to produce the desired effect, i.e., a composite picture of a face. In this prior device, the facial characteristics, i.e., noses, eyes, mouths etc are drawn and mounted on strips movable relative to each other so that the several strips may be selectively moved to build up a desired profile view of a face. Once again, there is no suggestion that corresponding front face views could be formed, nor is there any suggestion that the device would be useful for criminal identification purposes. The use of photographic parts for criminal identification purposes are not disclosed.

In still another prior known arrangement use has been made, in the formation of a front face view for criminal identification purposes, of a plurality of transparent sheets, each sheet bearing a facial characteristic such as a nose, a pair of eyes, a mouth etc. In the formation of a front face view, a plurality of such transparent sheets are laid one over the other so that all the facial characteristics are visible. Thus a composite picture is formed and should some characteristic of the formed face appear to be incorrect, the sheet carrying that facial characteristic is removed and replaced by a corresponding sheet carrying a different form of that facial characteristic. In this arrangement, the facial characteristics on said transparent sheets are line drawings, unlike photographic parts of the present invention and there is no suggestion, indeed it would be impossible, to form corresponding and accurate profile views using line drawings. The method and structure of this prior arrangement is totally different from that of the present application mainly due to the fact that line drawings are used in that system.

In yet another prior known device is a colour exhibiting device - utilises a front sheet and a back sheet adapted to be brought into superposed relation, the front sheet having a transparent section in which a room is depicted in perspective with substantially opaque coating material, the coating material being applied so as to leave substantially uncoated the visible areas of surfaces for which surface finishes are to be selected. Interchangeable cards are adapted to be slotted behind the front sheet so that surface appearances on the cards are visible through the transparent portion of the front sheet in order to establish whether a particular surface finish is suitable for the room.

There is no suggestion in this prior device that the same may utilise photographic parts, nor is there any suggestion that the device could be used for criminal identification purposes and indeed it is difficult to imagine it being used for such a purpose.

Finally, reference must be made to "wanted" posters in U.S. Post Offices, these "wanted" posters showing a known criminal or suspect both in front face and profile views. Because these "wanted" posters show a known person, the problem which I sought to solve is not be found, since no picture of a person need be assembled for comparison with a recollected face. The picture in the "wanted" posters is there and the only action necessary following a sight of the known person is the apprehension of that person.

There has been a long felt need for an identification system for criminal investigation purposes, and it was in answer to this long felt need that, after very many years of studying and investigating criminal investigation techniques I invented the system set forth in said U.S. pat. application Ser. No. 852,855 and set forth in the present application. An existing and well known identification system, exclusively used for criminal investigation purposes, was examined, and whilst I found that such identification system had some degree of success, its success rate left a lot to be desired in the way of crimes which had not been solved, and persons not identified and apprehended using this known identification system.

The failure of this known identification system was due largely, I believe, to the fact that it utilised line drawings and relied only on the building up of a front face view for the purposes of identification.

The creation of the various facial characteristics on the sheets used in such system were limited in their numbers, since variations of a common facial feature, when produced by line drawings, are small and not readily apparent and appreciated.

My identification system makes use of photographic parts each bearing a facial feature, and because the parts of my identification system are photographic even minor variations of the facial features are readily apparent and appreciated. These variations of the several facial features make possible the assembly of millions of facial appearances using the two assemblies of my identification system. The commercial success of my identification system has been extremely good, the system having been adopted and now in use by police forces in 22 countries of the world. The use of my identification system has led to the apprehension and conviction of a great many criminals throughout the world, many of the cases in which my system has been successfully used, commencing after only with a single witness to a crime who had seen the suspect only in front face view or in profile view but was able to generally describe some at least of the facial features of the person seen. The facial features of the person became clearer as the picture of the suspect was built up, the final picture being an extremely close resemblance to the person apprehended and in most cases convicted of the crime.

The success of my identification system has undoubtedly been due to the fact that photographic parts are used to display the several facial features. Unlike line drawings, photographs show very clearly modifications or variations in facial characteristics so that if, during the use of the assemblies of my identification system, a particular facial feature was thought to be not quite right by the person assembly or viewing the assembly of parts, that part could be quickly and easily substituted by another part on which the facial feature, though the difference is minor, made all the difference to the final picture of the assembly, for the person assembling the picture or viewing the assembly to say "that is the face I saw at the scene of the crime."

Many police forces in countries throughout the world where my identification system is used have expressed their delight with the success rate and the unexpected results of my identification system and have praised the system for the number of crimes which have been solved using my identification system. They have expressed a preference, by way of orders and re-orders for my identification system, over the known criminal identification systems.

My invention, in a first aspect, comprises a method of assembling a photographic representation of the facial features of a person recollected from the memory of an identifying person, the method comprising the steps of determining from an identifying person at least one basic facial characteristic of the recollected face, selecting from first and second pluralities of photographic parts a photographic representation of said basic facial characteristic, selecting from said first and second pluralities of photographic parts photographic representations of the remaining facial features of the recollected face, the photographic parts of said first and second pluralities each carrying indicia so that the selection of a photographic representation from one of said pluralities of photographic parts automatically enables the selection of the corresponding photographic representation from the other of said pluralities of photographic parts, and thereafter assembling said selected photographic representations in co-operating relationship so as to form first and second corresponding photographic assemblies of said recollected face, a first assembly of photographic representations comprising a front face head view and the second assembly of photographic representations comprising a profile view of said front face head view with the facial features in the first assembly being in the same geometric scale as those in the second assembly, said first assembly comprising a top facial frame bearing a representation of the top of the head, the forehead, the hair and the ears of the recollected person, a bottom frame bearing a representation of the lower cheeks and chin, separable intermediate parts fitting between said top frame and bottom frame and consisting of a representation of both eyes and upper nose, a representation of the lower nose parts including nostrils and tip and the inner parts of the cheek, and a representation of the mouth, said top facial frame having downwardly extending projections overlying side portions of said intermediate parts bearing the eyes and the lower nose representations, and the lower two of said intermediate parts occupying the top central portion of said bottom frame, said second profile assembly comprising a single top and side frame defining the top and one entire side edge which bears a representation in profile of the hair, the top of the head, the forehead, and an ear, and which defines part of the other side edge of the assembly, and second, third, fourth and fifth intermediate pieces, representing in sequence an eye on the second piece, a nose on the third piece which is positioned in front of the second piece to define a side extension at one edge thereof in common with the other side edge of the top profile frame, a mouth on the fourth piece and a chin on the fifth piece, said fourth and fifth pieces fitting to each other so as to join along a common edge meeting with the edge of the third piece, the indicia on each of said frames and intermediate pieces in the front face and profile assemblies identifying the facial features and permitting recording, in terms of these indicia, of the separate facial features assembled from the pluralities of photographic parts, to thereby provide a front and a corresponding profile total face which matches a recollected face.

In a second aspect my invention comprises an identification kit for use is assembling a photographic representation of the facial features of a person recollected from the memory of an identifying person, said identification kit comprising first and second pluralities of photographic parts each bearing a photographic representation of a facial feature, selected parts from said first and second pluralities being adapted to be placed in co-operating relationship so as to form first and second corresponding photographic assemblies of said recollected face, each of said parts of said first and second pluralities of parts carrying indicia so as to permit automatic selection of a corresponding part from one of said pluralities following the selection of a part from the other of said pluralities, a first assembly of photographic representations comprising a front face head view and the second assembly of photographic representations comprising a profile view of said front face head view with the facial features in the first assembly being in the same geometric scale as those in the second assembly, said first assembly comprising a top facial frame bearing a representation of the top of the head, the forehead, the hair and the ears of the recollected person, a bottom frame bearing a representation of the lower cheeks and chin, separable intermediate parts fitting between said top frame and bottom frame and consisting of a representation of both eyes and upper nose, a representation of the lower nose parts including nostrils and tip and the inner parts of the cheek, and a representation of the mouth, said top facial frame having downwardly extending projections overlying side portions of said intermediate parts bearing the eyes and the lower nose representations, and the lower two of said intermediate parts occupying the top central portion of said bottom frame, said second profile assembly comprising, a single top and side frame defining the top and one entire side edge which bears a representation in profile of the hair, the top of the head, the forehead, and an ear, and which defines part of the other side edge of the assembly, and second, third, fourth and fifth intermediate pieces, representing in sequence an eye on the second piece, a nose on the third piece which is positioned in front of the second piece to define a side extension at one edge thereof in common with the other side edge of the top profile frame, a mouth on the fourth piece and a chin on the fifth piece, said fourth and fifth pieces fitting to each other so as to join along a common edge meeting with the edge of the third piece, the indicia on each of said frames and intermediate pieces in the front face and profile assemblies identifying the facial features and permitting recording, in terms of these indicia, of the separate facial features assembled from the pluralities of photographic parts, to thereby provide a front and a corresponding profile total face which matches a recollected face.

Figure 2:
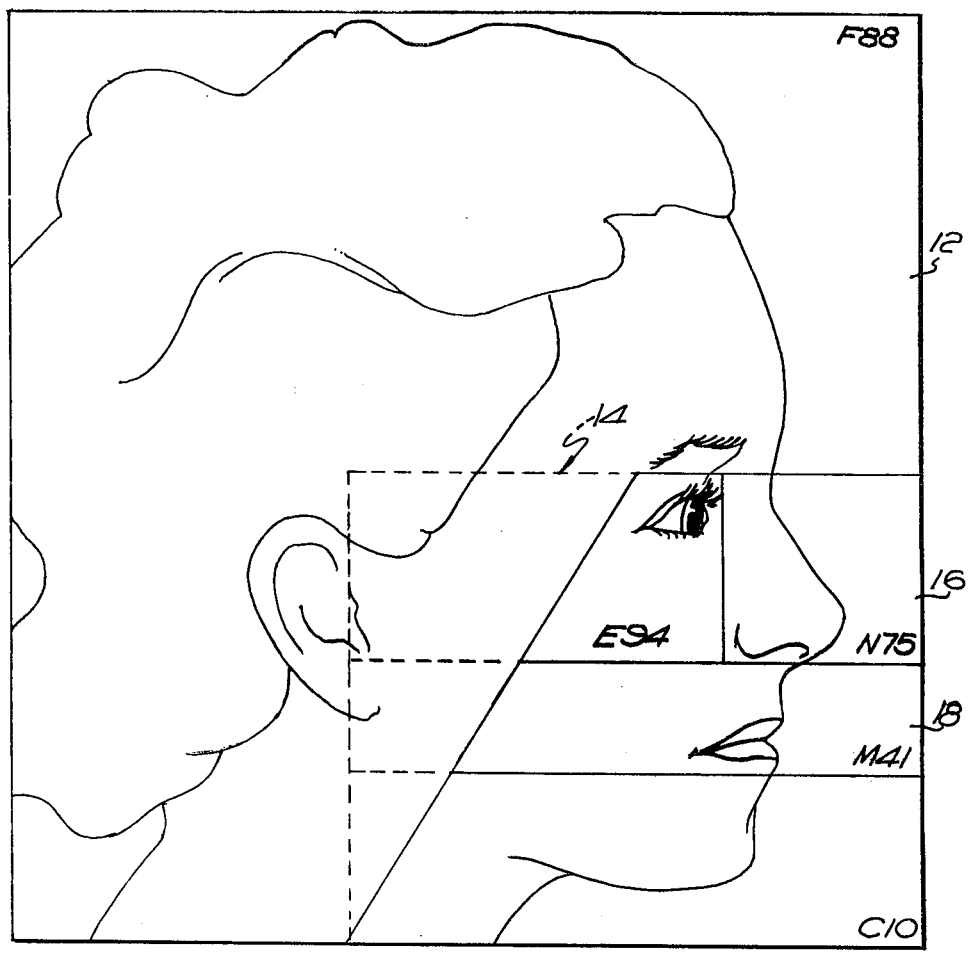

In order that the invention may be more readily understood, an embodiment thereof will now be described, by way of example, reference being made to the accompanying drawings, in which:

FIG. 1 is an illustration of a front face view composed according to the invention and using a plurality of photographic parts taken from a first assembly of pieces; and FIG. 2 is an illustration of a profile view, corresponding to the view illustrated in FIG. 1, composed according to the invention and using a plurality of photographic parts taken from a second assembly of pieces.

Referring to the drawings, and firstly to FIG. 1, the illustration represents a front view of a female human face assembled from a plurality of photographic parts, said parts having been selected from a larger plurality of parts by a person or persons making the identification.

The sub-assembly photograph of FIG. 1 is sectioned into five pieces - upper, intermediate and lower rectangular pieces 2, 4 and 6, and upper and lower facial framing pieces 8, 10. The upper, intermediate and lower pieces, 2, 4 and 6 respectively represent or comprise the eyes, eyebrows and the bridge of the nose, the main part of the nose (the nostrils and tip) and the inner parts of the cheeks, and the mouth. The upper facial framing piece 8 represents or comprises the forehead, hair and ears, whilst the lower facial framing piece 10 represents or comprises the outer parts of the cheeks and the chin.

It will be seen from FIG. 1 that when the array of pieces is in the co-operating relationship shown forming the required sub-assembly, the upper and lower facial framing pieces 8 and 10 overlie portions of the pieces 2, 4 and 6 and that the upper facial framing piece overlies the upper extremities of the lower facial framing piece 10.

It will be seen from the drawing that each of the five pieces 2, 4, 6, 8 and 10 have reference indicia thereon, the piece 2 having the reference "E94", the piece 4 having the reference "N75", the piece 6 having the reference "M41", the piece 8 having the reference "F88" and the piece 10 having the reference "C10", the prefix letters referring respectively to eyes, nose, mouth, forehead and chin.

The sub-assembly photograph of FIG. 2, like that of FIG. 1, also has five photographic pieces and represents a profile view of the face of FIG. 1, the several parts of the assembly of FIG. 2 exactly corresponding to the assembly of FIG. 1. The parts 12, 14, 16, 18 and 20 making up the assembly of FIG. 1 are selected from a second assembly of pieces by the person or persons making the identification.

The part 12 represents or comprises the forehead, hair and ear, and the second, third, fourth and fifth rectangular pieces 14, 16, 18 and 20 respectively represent or comprise an eye, the nose, the mouth, and the chin. It will be seen from FIG. 2 that when the parts 12, 14, 16, 18 and 20 are assembled in functional co-operating relationship, the piece 12 overlies portions of the pieces 14, 18 and 20 so as to maintain these pieces in the correct relationship. Thus as stated above, the assembly of FIG. 2 represents the profile view of the front face view of FIG. 1.

Like the photographic parts of FIG. 1, the photographic parts of FIG. 2 each have reference indicia thereon, this indicia corresponding to that on the photographic parts of FIG. 1.

These indicia on the parts selected and assembled into the photographic representations of FIGS. 1 and 2 permit, when a part has been selected for inclusion in say the front face view of FIG. 1, enable the automatic selection of the corresponding part for inclusion in the profile view of FIG. 2.

The photographic parts illustrated in FIG. 1 illustrate the several facial features in the same geometric scale as the facial features illustrated in FIG. 2.

A large number of front face views and profile views are sectioned into pieces in the manner described and illustrated in the drawings. Thus an identification kit in accordance with the invention will include a large selection of foreheads (with hair and ear(s)), a large selection of eyes, a large selection of noses, a large selection of mouths, and a large selection of chins, both in front face view and profile view, the corresponding parts in the front face view and the profile view being cross-referenced by the reference indicia such as is indicated in FIGS. 1 and 2 of the accompanying drawings.

Auxiliary identification pieces such as hats, glasses, beards and so on may also form part of the assembly.

In using my identification kit, in order to assemble a photographic representation of the facial features of a person recollected from the memory of an identifying person or identifying persons, it is firstly necessary that the identifying person describe and select at least one basic facial characteristic of the recollected face. It will be appreciated that there may be more than one identifying person who may each recall a particular facial characteristic, which may or may not be the same characteristic. When the basic facial characteristic or facial characteristics have been established, a part bearing that characteristic or characteristics is or are selected from one of said pluralities of photographic parts and placed in front of the identifying person(s). If it is not quite correct, then it is changed — as often as necessary — until the identifying person or persons is or are satisfied. When the basic characteristic(s) of the recalled face have been established to the satisfaction of the identifying person or person(s) — the basic clearly recalled characteristic might for example be the forehead and hair — then the identifying person will be asked about the type of eyes of the recalled face and again a part frame, one of the pluralities of parts — depending upon whether the identifying person saw the recalled face in front face view or in profile — will be selected and placed in correct relationship to that part first selected. This procedure is repeated in respect of the remaining facial feature until gradually the entire recalled face is assembled. It will be appreciated that many different selections may be made and changed during the course of assembling the recalled face.

If a front face view of the recalled face is assembled, then because of the indicia on the parts of the first and second pluralities of parts — the indicia will of course be on those parts of the assembly — the corresponding profile view may be assembled, the reference indicia enabling the automatic selection of the corresponding parts to form this profile view. This procedure may of course be carried out in reverse in that the profile view of the recalled face may be assembled first, followed by the assembly of the front face view.

The sub-assemblies of the front face and profile views may be arranged in a suitable frame housing which will enable the parts to be easily and conveniently changed during the course of assembling the recalled face, but such frame housing will not be described in this specification since it does not form part of the invention.

I claim:

1. A method of assembling a photographic representation of the facial features of a person recollected from the memory of an identifying person, the method comprising the steps of determining from an identifying person at least one basic facial characteristic of the recollected face, selecting from first and second pluralities of photographic parts a photographic representation of said basic facial characteristic, selecting from said first and second pluralities of photographic parts photographic representations of the remaining facial features of the recollected face, the photographic parts each carrying indicia so that the selection of a photographic representation from one of said pluralities of photographic parts automatically enables the selection of the corresponding photographic representation from the other of said pluralities of photographic parts, and thereafter assembling said selected photographic representations in co-operating and vertically adjustable relationship so as to form first and second corresponding photographic assemblies of said recollected face, a first assembly of photograpic representations comprising a front-face head view and the second assembly of photographic representations comprising a profile view of said front face head view with the facial features in the first assembly being in the same geometric scale as those in the second assembly said first assembly comprising a top facial frame bearing a representation of the top of the head, the forehead, the hair and the ears of the recollected person, a bottom frame bearing a representation of the lower cheeks and chin, separable intermediate parts fitting between said top frame and bottom frame and consisting of a representation of both eyes and upper nose, a representation of the lower nose parts including nostrils and tip and the inner parts of the cheek, and a representation of the mouth, said top facial framing member having downwardly extending projections overlying side portions of said intermediate parts bearing the eyes and the lower nose representations, and the lower two of said intermediate parts occupying the top central portion of said bottom frame, said second profile assembly comprising, a single top and side frame defining the top and one entire side edge which bears a representation profile of the hair, the top of the head, the forehead, and an ear, and which defines part of the other side edge of the assembly, and second, third, fourth and fifth intermediate pieces, representing in sequence an eye on the second piece, a nose on the third piece which is positioned in front of the second piece to define a side extension at one edge thereof in common with the other side edge of the top profile frame, a mouth on the fourth piece and a chin on the fifth piece, said fourth and fifth pieces fitting to each other so as to join along a common edge meeting with the edge of the third piece, the indicia on each of said frames and intermediate pieces in the front face and profile assemblies identifying the facial features and permitting recording, in terms of these indicia, of the separate facial features assembled from the pluralities of photographic parts, to thereby provide a front and a corresponding profile total face which matches a recollected face.

2. An identification kit for use in assembling a phtographic representation of the facial features of a person recollected from the memory of an identifying person, said identification kit comprising first and second pluralities of photographic parts each bearing a photographic representation of a facial feature, selected parts from said first and second pluralities being adapted to be placed in co-operating vertically adjustable relationship so as to form first and second corresponding photographic assemblies of said recollected face, each of said parts of said first and second pluralities of parts carrying indicia so as to permit automatic selection of a corresponding part from one of said pluralities following the selection of a part from the other of said pluralities, a first assembly of photographic representations comprising a front face head view and the second assembly of photographic representations comprising a profile view of said front face head view with the facial features in the first assembly being in the same geometric scale as those in the second assembly, said first assembly comprising a top facial frame bearing a representation of the top of the head, the forehead, the hair and the ears of the recollected person, a bottom frame bearing a representation of the lower cheeks and chin, separable intermediate parts fitting between said top frame and bottom frame and consisting of a representation of both eyes and upper nose, a representation of the lower nose parts including nostrils and tip and the inner parts of the cheek, and a representation of the mouth, said top facial framing member having downwardly extending projections overlying side portions of said intermediate parts bearing the eyes and the lower nose representations, and the lower two of said intermediate parts occupying the top central portion of said bottom frame, said second profile assembly comprising, a single top and side frame defining the top and one entire side edge whch bears a representation in profile of the hair, the top of the head, the forehead, and an ear, and which defines part of the other side edge of the assembly, and second, third, fourth and fifth intermediate pieces, representing in sequence an eye on the second piece, a nose on the third piece which is positioned in front of the second piece to define a side extension at one edge thereof in common with the other side edge of the top profile frame, a mouth on the fourth piece and a chin on the fifth piece, said fourth and fifth pieces fitting to each other so as to join along a common edge meeting with the edge of the third piece, the indicia on each of said frames and intermediate pieces in the front face and profile assemblies identifying the facial features and permitting recording, in terms of these indicia, of the separate facial features assembled from the pluralities of photographic parts, to thereby provide a front and a corresponding profile total face which matches a recollected face.

* * * * *